United States Patent
Hansson

(10) Patent No.: US 6,174,855 B1
(45) Date of Patent: Jan. 16, 2001

(54) PHARMACEUTICAL COMPOSITIONS COMPRISING THROMBIN INHIBITORS AND THEIR USE IN THE CONTROL OF WOUND HEALING PROCESSES

(75) Inventor: Hans-Arne Hansson, Hovås (SE)

(73) Assignee: AstraZeneca AB, Sodertalje (SE)

( * ) Notice: Under 35 U.S.C. 154(b), the term of this patent shall be extended for 0 days.

(21) Appl. No.: 09/101,351

(22) PCT Filed: Jan. 16, 1997

(86) PCT No.: PCT/SE97/00057

§ 371 Date: Jul. 7, 1998

§ 102(e) Date: Jul. 7, 1998

(87) PCT Pub. No.: WO97/25994

PCT Pub. Date: Jul. 24, 1997

(30) Foreign Application Priority Data

Jan. 18, 1996 (SE) .................................................... 9600216

(51) Int. Cl.⁷ ...................... A61K 38/00; A61K 31/715
(52) U.S. Cl. .................... 514/2; 514/12; 514/21; 514/54; 514/55; 514/802; 530/380; 530/382
(58) Field of Search ................... 514/2, 12, 21, 514/54, 55, 802; 530/380, 382

(56) References Cited

U.S. PATENT DOCUMENTS

| 4,532,134 | * | 7/1985 | Malette et al. ......................... 514/55 |
| 5,116,824 |   | 5/1992 | Miyata et al. ........................... 514/55 |
| 5,192,689 | * | 3/1993 | Hemker et al. ......................... 436/69 |
| 5,209,776 |   | 5/1993 | Bass et al. ............................. 106/124 |
| 5,792,835 | * | 8/1998 | Tse et al. ............................... 530/382 |

FOREIGN PATENT DOCUMENTS

| 0051354 | * | 5/1982 | (EP) . |
| 0426368 | * | 5/1991 | (EP) . |
| 9115233 |   | 10/1991 | (WO) . |
| 9312801 |   | 7/1993 | (WO) . |

* cited by examiner

Primary Examiner—Christopher S. F. Low
Assistant Examiner—Abdel A. Mohamed
(74) Attorney, Agent, or Firm—White & Case LLP

(57) ABSTRACT

There is provided the use of a thrombin inhibitor in the manufacture of a product for use in the control of wound healing processes within the body, in particular, the inhibition or prevention of fibrin-related adhesion and/or scar tissue formation, as well as products for use in the control of wound healing processes within the body comprising polysaccharides (e.g., chitosans) and low molecular weight peptide-based thrombin inhibitors.

33 Claims, No Drawings

PHARMACEUTICAL COMPOSITIONS COMPRISING THROMBIN INHIBITORS AND THEIR USE IN THE CONTROL OF WOUND HEALING PROCESSES

FIELD OF THE INVENTION

This invention relates to the use of known pharmaceutically-active compounds in the manufacture of a product for use in the control of wound healing processes within the body, in particular in the prevention of adhesions, and/or the formation of scar tissue, resulting from physical trauma, including injury, surgery and burns, as well as from inflammation; and further to pharmaceutical products for use in the control of wound healing processes within the body.

BACKGROUND TO THE INVENTION

The relative mobility of many organs of the human body is a prerequisite of optimal function. In this respect, it is important that such organs are able to move and slide in relation to adjacent organs and/or in relation to the body cavities within which they are enclosed. For example, if the oesophagus, the stomach, the intestines, the liver and the urogenital organs were not at least partially mobile in relation to adjacent organs and the abdominal wall and the diaphragm, functional disturbances would occur, such as the restriction of respiratory movement, hampered movement of intra-abdominal structures, intestinal obstruction and/or infertility.

If an organ receives a physical trauma, such as an injury, surgery, a burn or an electric shock, or experiences inflammation as a result of a pathogenic cause, one of the inevitable consequences of the healing and inflammatory processes which follow is the formation of adhesions and scar tissue, which may naturally restrict the aforementioned organ mobility.

Adhesions and scar tissue are formed as a result of the formation of a fibrin-platelet network following physical trauma or pathogenic inflammation, and the subsequent rebuilding and replacement of this network by granulation tissue.

The complex and typically highly irregular structure of the fibrin-platelet network, formed at an early stage after the trauma or as a result of inflammation, is of key importance in the fate of any wound healing process. Any physical structure, particularly filaments and membranes, whether diffusely or distinctly outlined, acts as a guide for the invading granulation tissue. This newly formed tissue is, in accordance with the mechanism described above, eventually rebuilt as scar tissue, organised as fibrous strands or membranes. The invading granulation tissue cells can practically never fully substitute for the original cells and, as a result, the tissue is never regenerated, but merely repaired. This is true for both the skin and for mucosal membranes, including those lining the body cavities, as well as other structures including muscles, tendons and nerves. Moreover, the scar tissue so formed may, in time, contract and remain contracted, deforming and disorganising the injured area.

The proliferation and invasion of fibrin threads by even a few granulation tissue cells (including angiogenic cells) is usually sufficient to induce the formation of adhesions. The direction, density and organization of the individual fibrin threads in the fibrin-platelet network of the clot provides information, and determines the track to be taken by the invading granulation tissue cells, as well as by specific cells such as Schwann cells. Extracellular fibrin may deposit, stick to and establish abnormal bridges between adjacent structures.

Thus, the structure of the fibrin-platelet network is of key importance in guiding the invading granulation tissue and thus in the formation of adhesions and scar tissue.

PRIOR ART

European Patent Application EP 0 051 354 describes a polymeric substrate coated with the polysaccharide chitosan, to which is appended the antithrombotic agent heparin.

U.S. Pat. No. 5,116,824 describes a composite material comprising an N-acylchitosan and collagen which is suitable for wound dressings. Heparin may be incorporated as an antithrombotic agent.

Neither of these prior art documents disclose the use of the devices described therein in the prevention of the formation of adhesions and/or scar tissue following physical trauma, such as injury or surgery or pathogenic inflammation. Moreover, the use of thrombin inhibitors, and in particular low molecular weight thrombin inhibitors, is not mentioned.

Further, the combined use of fibrinolytic agents and polysaccharides has been neither disclosed nor suggested to be of potential in the prevention of formation of adhesions and/or scar tissue.

DISCLOSURE OF THE INVENTION

We have now found, surprisingly, that thrombin inhibitors significantly inhibit or prevent the formation of adhesions and/or scar tissue following physical trauma or pathogenic inflammation, and may thus be used in the control of wound healing processes within the body.

According to a first aspect of the invention there is provided the use of a thrombin inhibitor in the manufacture of a product for use in the control of wound healing processes within the body.

In particular, we have found that thrombin inhibitors may be used to inhibit or prevent fibrin-related adhesion and/or scar tissue formation as a result of physical trauma or pathogenic inflammation.

By "fibrin-related adhesion" we mean adhesion resulting from the establishment of a fibrin-platelet network (i.e. a network of fibrin and cells including platelets) following a physical trauma or pathogenic inflammation, as described hereinbefore.

We have found that thrombin inhibitors may be used to inhibit or prevent the formation of fibrin-related adhesion and/or scar tissue following physical trauma, including physical injury to the skin or the internal organs, including accidental injury; surgery, including laparoscopic surgery, "open" conventional gastrointestinal and gynaecological surgery, oncological surgery, orthopaedic surgery (e.g. treatment of fractures, implantation of a prosthesis, surgery on tendons, muscles and ligaments), neurosurgery, heart and chest surgery or trauma surgery and the insertion of catheters; thermal trauma, including burns; chemical trauma, including exposure to corrosive, acidic or alkaline substances; and electrical shock.

Moreover, we have found that thrombin inhibitors may be used to inhibit or prevent the formation of fibrin-related adhesion and/or scar tissue resulting from pathogenic inflammation, including inflammation produced as a result of medical conditions, such as rheumatoid diseases, systemic inflammatory reactions and autoimmune diseases.

According to a further aspect of the invention, there is provided a method of inhibition or prevention of fibrin-related adhesion and/or scar tissue formation, which method comprises administration of a thrombin inhibitor to a patient in need of such inhibition or prevention.

In the case of surgery, or pathogenic inflammation, "administration" may take place before, after or during the surgical event or the onset of the medical condition as appropriate.

The thrombin inhibitor may be administered either locally or systemically, in the form of pharmaceutical preparations comprising the thrombin inhibitor in a pharmaceutically acceptable dosage form. Dosage forms which may be employed for local and systemic administration include those which are well known to those skilled in the art, for example as described in Lachman et al, "*Theory and Practice of Industrial Pharmacy*", Lea & Febiger (1986).

By "pharmaceutically acceptable dosage form" we mean a dosage form which is sterile and, preferably, non-pyrogenic.

In particular, we have found that the co-administration of a polysaccharide and a thrombin inhibitor results in the inhibition or prevention of fibrin-related adhesion and/or scar tissue formation when compared to administration of the polysaccharide alone.

Thus, according to a further aspect of the invention there is provided a method of inhibition or prevention of fibrin-related adhesion and/or scar tissue formation, which method comprises the co-administration of a polysaccharide and a thrombin inhibitor to a patient in need of such inhibition or prevention.

The thrombin inhibitor may be co-administered with the polysaccharide either locally or systemically. Moreover co-administration may take place separately, i.e. by independently administering the thrombin inhibitor before, after, or at the same time as, the polysaccharide, by an appropriate means, for example, in the case of local application, by administering or infusing a solution of thrombin inhibitor via a polysaccharide product. Alternatively, in the case of local application, the thrombin inhibitor may be anchored to the polysaccharide by an appropriate means, e.g. by impregnation, or physical or chemical bonding.

Suitable thrombin inhibitors for use in the inhibition or prevention of fibrin-related adhesion and/or scar tissue include hirudin and hirudin fragments (i.e. those with at least the last 8 carboxyterminal amino acids, e.g. the fragment consisting of the last C-terminal amino acids of the known sequence in hirudin), biosynthetic analogues of hirudin (e.g. those with up to 10 to 12 amino acids, some of which are commercially available), the protein NAPc2, and low molecular weight peptide-based thrombin inhibitors.

Preferred thrombin inhibitors include low molecular weight peptide-based thrombin inhibitors. The term "low molecular weight peptide-based thrombin inhibitors" will be well understood by one skilled in the art to include thrombin inhibitors with one to four peptide linkages, and/or with a molecular weight below 1000, and includes those described in the review paper by Claesson in Blood Coagul. Fibrin. (1994) 5, 411, as well as those disclosed in U.S. Pat. No. 4,346,078; International Patent Applications WO 93/11152, WO 95/23609, WO 95/35309, WO 96/25426, WO 94/29336, WO 93/18060 and WO 95/01168; and European Patent Applications 648 780, 468 231, 559 046, 641 779, 185 390, 526 877, 542 525, 195 212, 362 002, 364 344, 530 167, 293 881, 686 642, 669 317 and 601 459.

Preferred low molecular weight peptide-based thrombin inhibitors include those known collectively as the "gatrans". Particular gatrans which may be mentioned include HOOC—$CH_2$—(R)Cha-Pic-Nag-H (known as inogatran; see International Patent Application WO 93/11152 and the list of abbreviations therein) and HOOC—$CH_2$—(R)Cgl-Aze-Pab-H (known as melagatran; see International Patent Application WO 94/29336 and the list of abbreviations therein). Particularly preferred thrombin inhibitors include melagatran.

In the inhibition or prevention of the formation of fibrin-related adhesions and/or scar tissue, suitable doses of thrombin inhibitors will depend upon the thrombin inhibitor which is used, the severity of the disorder to be treated, the nature of the patient to be treated and the route of administration. Suitable doses are those which give a mean plasma concentration in the range 0.001 to 100 μmol/L, preferably, 0.005 to 20 μmol/L and particularly 0.009 to 15 μmol/L over the period for which treatment is required. Suitable doses for inogatran are those which give a mean plasma concentration in the range 0.1 to 10 μmol/L, and preferably 0.5 to 2 μmol/L; suitable doses for melagatran are those which give a mean plasma concentration in the range 0.01 to 5 μmol/L, and preferably 0.1 to 1 μmol/L.

None of the low molecular weight peptide-based thrombin inhibitors, including inogatran and melagatran, have to the Applicant's knowledge previously been reported to affect the activation and aggregation of thrombocytes, and therefore the formation of scar tissue and connective tissue adhesions.

Thus according to a further aspect of the invention there is provided the use of a low molecular weight peptide-based thrombin inhibitor in the prevention or reduction of the activation and aggregation of thrombocytes.

We have also found that application of a fibrinolytic agent, in addition to, or instead of, a thrombin inhibitor, also results in the inhibition or prevention of fibrin-related adhesion and/or scar tissue formation. In particular, we have found that co-application of a polysaccharide and a fibrinolytic agent, in addition to, or instead of, a thrombin inhibitor, also results in the inhibition or prevention of fibrin-related adhesion and/or scar tissue formation.

Examples of fibrinolytic agents which may be employed include plasminogen activators (tPA), streptokinase and urokinase.

Suitable polysaccharides which may be employed include those which are suitable for the control of wound healing processes, for example those which will be recognised by the person skilled in the art as being capable of being manufactured in the physical forms described below, thus facilitating the application of the polysaccharide to a wound. Particular polysaccharides which may be mentioned include chitosans, hyaluronans, chondroitin sulphates, dermatan sulphates, keratan sulphates and heparan sulphates. Preferred polysaccharides include chitosans.

The polysaccharides may be manufactured in a variety of physical forms, depending upon the part of the body to be treated, in accordance with techniques which are well known to those skilled in the art. Physical forms which may be mentioned include films, membranes, gels, solutions, threads, rods or tubes in any dimension. However, we prefer the polysaccharide to be in the form of a film, a membrane or a gel.

According to a further aspect of the invention there is thus provided a pharmaceutical product comprising a polysaccharide and a low molecular weight peptide-based thrombin inhibitor.

The products as defined herein have the advantage that they significantly inhibit and/or prevent the formation of fibrin-related adhesions and/or scar tissue, as described below. The products may also have the advantage that they may be more effective than, produce fewer side effects than, or that they may have other useful pharmacological properties over, similar products known in the prior art.

The invention is illustrated, but in no way limited, by way of the following examples. Table 1 illustrates the inhibition of fibrin related adhesion using the thrombin inhibitor, inogatran.

EXAMPLES

Animal experiments were performed in accordance with ethical permissions O 68/95; 69/95 & 70/95 granted by the Animal Experiments Ethical Committee at the University of Gothenberg.

Example 1

The induction of an injury to the serosal surface of the stomach of an adult, anaesthetised rat by the exposure of an area of 7 mm diameter to 80% acetic acid over 60 seconds repeatedly resulted in the formation of strong and extensive adhesions, connecting and firmly anchoring the stomach with the intestine, the omentum, the liver and, less commonly, the spleen.

Example 2

The serosal surface of the stomach of an adult, anaesthetised rat was exposed in an area of 7 mm diameter to 80% acetic acid over 60 seconds. After rinsing with buffered saline, the area was covered with a chitosan membrane or, in an alternative experiment, a gel, having a diameter several millimeters larger than the injured area. It was observed that the number and dimensions of the adhesions formed, bridging to the liver, intestines and the omentum, were reduced.

Example 3

The serosal surface of the stomach of an adult, anaesthetised rat was exposed in an area of 7 mm diameter to 80% acetic acid over 60 seconds. After rinsing with buffered saline solution, the area was covered with a chitosan membrane or, in an alternative experiment, a gel, with a diameter several millimeters larger than that of the injured area. 100 µL of a solution of the thrombin inhibitor HOOC—CH$_2$—(R)Cgl-Aze-Pab-H (melagatran; 100–500 µg/mL, dissolved in phosphate buffered saline solution) was dripped daily onto the membrane. In all cases, absolutely no bridging tissue, i.e. adhesions due to replacement of fibrin strands by granulation tissue, were formed between the stomach and the liver, the intestines and the omentum after 2 to 5 days.

Example 4

The serosal surface of the stomach of an adult, anaesthetised rat was exposed in an area of 7 mm diameter to 80% acetic acid over 60 seconds. After rinsing with buffered saline solution, an osmotic minipump (Alza 2001, volume about 220 µL; pumping rate about 1 µL/h; Alza Corp.; Palo Alto, Calif., USA; prefilled with a solution of melagatran, 2–100 µg/mL) was implanted into the peritoneal cavity delivering 100 µL of solution over almost a week. In all cases, only scattered, delicate adhesions of fibrin, platelets and other blood cells, and of newly formed granulation tissue were formed between the stomach and the liver, the intestines and the omentum during following up to 10 days' treatment; the occasional, large bundle of granulation tissue could be recognized.

Example 5

The serosal surface of the stomach of an adult, anaesthetised rat was exposed in an area of 7 mm diameter to 80% acetic acid over 60 seconds. After rinsing with buffered saline solution, an osmotic minipump (Alza 2001, volume about 220 µL; pumping rate about 1 µL/h; Alza Corp.; Palo Alto, Calif., USA; prefilled with a solution of the thrombin inhibitor melagatran, 2–100 µg/mL) was implanted into the peritoneal cavity and delivered 100 µL of solution over a week, with the outlet of the pump connected to a chitosan membrane or, in an alternative experiment, a gel, having a diameter several millimeters larger than the injured area. No fibrin network or strands of granulation tissue could be detected between the stomach and the liver, the intestines and the omentum over observation periods of up to 10 days.

Example 6

The serosal surface of the stomach of an adult anaesthetised rat was exposed in an area of 7 mm diameter to 80% acetic acid over 60 seconds. After rinsing with buffered saline solution, an osmotic minipump (Alza 2001, volume about 220 µL; pumping rate about 1 µL/h; Alza Corp.; Palo Alto, Calif., USA; prefilled with a solution of the thrombin inhibitor melagatran, 2–100 µg/mL) was implanted into the peritoneal cavity, with the outlet of the pump kept open, and delivered its content into the abdominal cavity. The wounded area was covered by a chitosan membrane or, in an alternative experiment, a gel, having a diameter several millimeters larger than that of the injured area. No fibrin network, nor any strands of granulation tissue, could be detected between the stomach and the liver, the intestines and the omentum over observation periods of up to 10 days.

Example 7

The serosal surface of the stomach of an adult, anaesthetised rat was exposed in an area of 7 mm diameter to 80% acetic acid over 60 seconds. After rinsing with buffered saline, the wounded area was covered by a chitosan membrane or, in an alternative experiment, a gel, having a diameter several millimeters larger than the injured area. An osmotic minipump (Alza 2001, volume about 220 µL; pumping rate about 1 µL/h; Alza Corp.; Palo Alto, Calif., USA; prefilled with a solution of the thrombin inhibitor melagatran, 2–100 µg/mL) was implanted subcutaneously, with the outlet of the pump kept open, delivering its content into the adjacent tissue. No fibrin network, nor any strands of granulation tissue, could be detected between the stomach and the liver, the intestines and the omentum during observation periods of up to 14 days.

Example 8

The serosal surface of the stomach of an adult, anaesthetised rat was exposed in an area of 7 mm diameter to 80% acetic acid over 60 seconds. After rinsing with buffered saline solution, the wounded area was covered by a chitosan membrane or, in an alternative experiment, a gel, with a diameter several millimeters larger than the injured area. An osmotic minipump (Alza 2001, volume about 220 µL; pumping rate about 1 µL/h;

Alza Corp.; Palo Alto, Calif., USA; prefilled with a solution of streptokinase, purchased from Sigma Chemical Co, St. Louis, Mo., USA) was implanted in the peritoneal cavity, with the outlet of the pump connected with, and opening onto, the surface of the chitosan membrane. No fibrin-platelet network nor any strands of granulation tissue could be detected between the stomach and the liver, the intestines and the omentum during observation periods of up to 10 days.

Example 9

The serosal surface of the stomach of an adult, anaesthetised rat was exposed in an area of 7 mm diameter to 80% acetic acid over 60 seconds. After rinsing with buffered saline, the wounded area was covered by a chitosan membrane or, in an alternative experiment, a gel, having a diameter several millimeters larger than the injured area. An osmotic minipump (Alza 2001, volume about 220 µL; pumping rate about 1 µL/h; Alza Corp.; Palo Alto, Calif., USA; prefilled with a solution of streptokinase, purchased from Sigma Chemical Co, St Louis, Mo., USA) was implanted in the abdominal cavity with the outlet of the pump kept free and open. No fibrin network, nor any strands of newly formed granulation tissue, could be detected connecting the stomach with the liver, the intestines and the omentum during an observation period of up to 10 days.

Example 10

The serosal surface of the stomach of an adult, anaesthetised rat was exposed in an area of 7 mm diameter to 80% acetic acid over 60 seconds. After rinsing with buffered saline the wounded area was covered by a chitosan membrane having a diameter several millimeters larger than that of the injured area. An osmotic minipump (Alza 2001, volume about 220 µL; pumping rate about 1 µL/h; Alza Corp.; Palo Alto, Calif., USA; prefilled with a solution of Actilyse® (recombinant human tissue-plasminogen-activator; Boehringer Ingelheim)) was implanted in the abdominal cavity with the outlet of the pump kept free and open. No fibrin network, nor any strands of newly formed granulation tissue, could be detected connecting the stomach with the liver, the intestines and the omentum during an observation period of up to 10 days.

Example 11

An incision was made in the thigh through the skin into the muscle tissue in an anaesthetised adult rat, and the muscle fascia was surgically removed in a defined area (about 10×15 mm). The wound was sutured, and eventually opened for inspection after 10 days. Numerous adhesions were recognized, and the presence of granulation tissue were noticed to connect and lock the injured area to adjacent muscles, muscle fascia, vessels and nerves as well as to the skin.

Example 12

An incision was made in the thigh through the skin into the muscle tissue in an anaesthetised adult rat and the muscle fascia was surgically removed in a defined area (about 10×15 mm). The muscle fascia was covered by a chitosan membrane or, in an alternative experiment, a gel, to which was connected a tube from an osmotic minipump, which had been implanted subcutaneously (Alza 2001, total volume about 220 µL; pumping rate about 1 µL/h; Alza Corp.; Palo Alto, Calif., USA; prefilled with a solution of the thrombin inhibitor melagatran, 0.2×100µg/mL). The wound was then sutured, and eventually opened and inspected after 10 days. The severity and dimensions of the adhesions formed between adjacent structures were strikingly reduced. Granulation tissue was present to a roughly normal extent and distribution, but was largely not connecting and did not lock the injured area to adjacent muscles, muscle fascia, vessels and nerves or the skin, when compared to that observed in untreated animals, and as described in Example 11 above.

Example 13

The serosal surfaces of the stomachs of adult, anaesthetised rats were exposed in an area 7 mm diameter to 80% acetic acid over 60 seconds and then rinsed with buffered saline. One or more osmotic minipumps (Alza 2001, volume about 220 µL; pumping rate about 1 µL/h; or Alza 2ML1, volume about 2000 µL; pumping rate about 10 µL/h; Alza Corp.; Palo Alto, Calif., USA; prefilled with a solution of the thrombin inhibitor inogatran , 65.86 µg/µL) were implanted into the peritoneal cavity for a week and the outlet of the pump being positioned free in the peritoneal cavity adjacent to the injured area. No fibrin network or strands of granulation tissue could be detected between the stomach and the liver, the intestines and the omentum during observation periods of up to 10 days, at plasma concentrations of at least 0.5 µmol/L (see Table 1). Thus, the formation of adhesions was prevented in a dose-response related manner.

Example 14

The serosal surfaces of the stomachs of adult, anaesthetised rats were exposed in an area of 7 mm diameter to 80 % acetic acid over 60 seconds and then rinsed with buffered saline. The wounded area of each animal was covered by a hyaluronan or chitosan membrane having a diameter several millimeters larger than the injured area. One osmotic minipump (Alza 2001, volume about 220 µL; pumping rate about 1 µL/h; Alza Corp.; Palo Alto, Calif., USA; prefilled with a solution of the thrombin inhibitor hirudin (Sigma Chemical Co., St. Louis, Mo., USA)) per animal was implanted into the peritoneal cavity for a week. The outlet of the pump positioned in the peritoneal cavity adjacent to the injured area and its polysaccharide covering. No fibrin network or strands of granulation tissue could be detected between the stomach and the liver, the intestines and the omentum during observation periods of up to 10 days.

Example 15

The serosal surfaces of the stomachs of six adult, anaesthetised rats were exposed in an area of 7 mm diameter to 80% acetic acid over 60 seconds and then rinsed with buffered saline. The wounded area was covered by a hyaluronan or chitosan membrane having a diameter several millimeters larger than the injured area. An osmotic minipump (Alza 2001, volume about 220 µL; pumping rate about 1 µL/h; Alza Corp.; Palo Alto, Calif., USA; prefilled with a solution of hirudin fragments (fragment consisting of the last C-terminal amino acids of the known sequence in hirudin); Sigma Chemical Co., St. Louis, Mo., USA) was implanted into the peritoneal cavity for a week and the outlet of the pump positioned in the peritoneal cavity adjacent to the injured area and its polysaccharide covering. No fibrin network or strands of granulation tissue could be detected between the stomach and the liver, the intestines and the omentum during observation periods of up to 10 days in any of the animals.

TABLE 1

Results for Inogatran

| Rat id/ Day of Anal. | Rat Weight g | Infusion Rate µL/h | Dose µg/h | Dose µg/kg/h | Plasma Conc. µmol/L | Adherences score | Mean Plasma Conc. µmol/L |
|---|---|---|---|---|---|---|---|
| 163/1 | 532 | 1*1 | 66 | 124 | 0.58 | | |
| 2 | | | | | 0.30 | | |
| 7 | | | | | 0.17 | 3 | |
| 163/1 | 466 | 1*1 | 66 | 142 | 0.61 | | |
| 2 | | | | | 0.14 | | |

TABLE 1-continued

Results for Inogatran

| Rat id/<br>Day of<br>Anal. | Rat<br>Weight<br>g | Infusion<br>Rate<br>µL/h | Dose<br>µg/h | Dose<br>µg/kg/h | Plasma<br>Conc.<br>µmol/L | Ad-<br>her-<br>ences<br>score | Mean<br>Plasma<br>Conc.<br>µmol/L |
|---|---|---|---|---|---|---|---|
| 7 | | | | | 0.19 | 4 | 0.18 |
| 163/1 | 491 | 2*1 | 132 | 269 | 0.47 | | |
| 2 | | | | | 0.35 | | |
| 7 | | | | | 0.24 | 2 | |
| 164/1 | 532 | 2*1 | 132 | 248 | 0.46 | | |
| 2 | | | | | 0.79 | | |
| 7 | | | | | 0.37 | 2 | 0.31 |
| 165/1 | 449 | 4*1 | 264 | 588 | 1.27 | | |
| 2 | | | | | 0.47 | | |
| 7 | | | | | 0.57 | 0 | |
| 166/1 | 473 | 4*1 | 264 | 558 | 0.81 | | |
| 2 | | | | | 0.89 | | |
| 7 | | | | | 0.87 | 1 | 0.72 |
| 169/1 | 496 | 1*10 | 658 | 1327 | 2.52 | | |
| 2 | | | | | 2.11 | | |
| 7 | | Minor Tendency to Bleed | | | 1.88 | 0 | |
| 171/1 | 487 | 1*10 | 658 | 1351 | 1.13 | | |
| 2 | | | | | 4.23 | | |
| 7 | | Minor Tendency to Bleed | | | 1.79 | 0 | 1.84 |
| 170/1 | 477 | 2*10 | 1317 | 2761 | 4.44 | | |
| 2 | | | | | 2.82 | | |
| 7 | | Diffuse Bleeding, reduced red blood cells ratio | | | 5.56 | 0 | |

In all cases, the concentration of inogatran in solution was 65.85 µg/µL.

What is claimed is:

1. A method of controlling wound healing processes within the body, which method comprises administration an effective amount of an active agent selected from the group consisting of hirudin, a hirudin fragment, a low molecular weight peptide-based thrombin inhibitor or a fibrinolytic agent to a patient in need of such control for a time and under conditions sufficient to control wound healing processes within the body.

2. A method of inhibition or prevention of fibrin-related adhesion, which method comprises administration an effective amount of an active agent selected from the group consisting of hirudin, a hirudin fragment, a low molecular weight peptide-based thrombin inhibitor or a fibrinolytic agent to a patient in need of such inhibition for a time and under conditions sufficient to inhibit fibrin-related adhesion.

3. A method of inhibition an effective amount of scar tissue formation, which method comprises administration of an active agent selected from the group consisting of hirudin, a hirudin fragment, a low molecular weight peptide-based thrombin inhibitor or a fibrinolytic agent to a patient in need of such inhibition for a time and under conditions sufficient to inhibit scar tissue formation.

4. A method as claimed in any one of claims 1–3, wherein the method comprises the co-administration of a polysaccharide with the hirudin, the hirudin fragment, the low molecular weight peptide-based thrombin inhibitor or the fibrinolytic agent.

5. A method as claimed in claim 1, 2, or 3, wherein the low molecular weight peptide-based thrombin inhibitor is a gatran.

6. A method as claimed in claim 5, wherein the low molecular weight peptide-based thrombin inhibitor is inogatran or melagatran.

7. A method as claimed in claim 6, wherein the low molecular weight peptide-based thrombin inhibitor is melagatran.

8. A method as claimed in claim 4, wherein the polysaccharide is a chitosan.

9. A method as claimed in claim 4, wherein the low molecular weight peptide-based thrombin inhibitor is a gatran.

10. A method as claimed in claim 9, wherein the low molecular weight peptide-based thrombin inhibitor is inogatran or melagatran.

11. A method as claimed in claim 10, wherein the low molecular weight peptide-based thrombin inhibitor is melagatran.

12. A method as claimed in claim 8, wherein the low molecular weight peptide-based thrombin inhibitor is a gatran.

13. A method as claimed in claim 12, wherein the low molecular weight peptide-based thrombin inhibitor is inogatran or melagatran.

14. A method as claimed in claim 13, wherein the low molecular weight peptide-based thrombin inhibitor is melagatran.

15. A method of reduction of the activation and aggregation of thrombocytes which method comprises an effective amount administration of a low molecular weight peptide-based thrombin inhibitor to a patient in need of such prevention or for a time and under conditions sufficient to reduce the activation and aggregation of thrombocytes.

16. A method of controlling wound healing processes within the body, which method comprises coadministration an effective amount of a fibrinolytic agent with a thrombin inhibitor selected from the group consisting of hirudin, a hirudin fragment and a low molecular weight peptide-based thrombin inhibitor to a patient in need of such control for a time and under conditions sufficient to control wound healing processes within the body.

17. A method of inhibition of fibrin-related adhesion, which method comprises coadministration an effective amount of a fibrinolytic agent with a thrombin inhibitor selected from the group consisting of hirudin, a hirudin fragment and a low molecular weight peptide-based thrombin inhibitor to a patient in need of such inhibition for a time and under conditions sufficient to inhibit fibrin-related adhesion.

18. A method of inhibition of scar tissue formation, which method comprises coadministration an effective amount of a fibrinolytic agent with a thrombin inhibitor selected from the group consisting of hirudin, a hirudin fragment and a low molecular weight peptide-based thrombin inhibitor to a patient in need of such inhibition for a time and under conditions sufficient to inhibit scar tissue formation.

19. A method as claimed in any one of claims 16 to 18, wherein the method comprises the further coadministration of a polysaccharide.

20. A method as claimed in any one of claims 16 to 18, wherein the fibrinolytic agent is selected from the group consisting of a plasminogen activator, a streptokinase and a urokinase.

21. A method as claimed in claim 19, wherein the fibrinolytic agent is selected from the group consisting of a plasminogen activator, a streptokinase and a urokinase.

22. A pharmaceutical composition comprising a polysaccharide and a low molecular weight peptide-based thrombin inhibitor.

23. A composition as claimed in claim 22, wherein the thrombin inhibitor is a gatran.

24. A composition as claimed in claim 23, wherein the thrombin inhibitor is inogatran or melagatran.

25. A composition as claimed in claim 24, wherein the thrombin inhibitor is melagatran.

26. A composition as claimed in any one of claims 22 to 25 further comprising a fibrinolytic agent.

27. A composition as claimed in any one of claims 22 to 25, wherein the low molecular weight peptide-based thrombin inhibitor is infused via the polysaccharide.

28. A composition as claimed in any one of claims 22 to 25, wherein the polysaccharide is in the form of a film, membrane or gel.

29. A composition as claimed in claim 28, wherein the low molecular weight peptide-based thrombin inhibitor is infused via the polysaccharide.

30. A composition as claimed in any one of claims 22 to 25, wherein the polysaccharide is a chitosan.

31. A composition as claimed in claim 30, wherein the low molecular weight peptide-based thrombin inhibitor is infused via the polysaccharide.

32. A composition as claimed in claim 30, wherein the polysaccharide is in the form of a film, membrane or gel.

33. A composition as claimed in claim 32, wherein the low molecular weight peptide-based thrombin inhibitor is infused via the polysaccharide.

* * * * *

UNITED STATES PATENT AND TRADEMARK OFFICE
CERTIFICATE OF CORRECTION

PATENT NO. : 6,174,855 B1  Page 1 of 1
DATED : January 16, 2001
INVENTOR(S) : Hansson It is certified that error appears in the above-identified patent and that said Letters Patent is hereby corrected as shown below:

Column 1,
Line 5, between the title and the heading "Field of the Invention", insert:
-- This application is the National Stage of International Application No. PCT/SE97/00057, filed January 16, 1997. --

Column 9,
Line 32, insert -- of -- after "administration".
Line 39, delete "or prevention".
Line 40, insert -- of -- after "administration".
Line 45, delete "an effective amount".
Line 46, insert -- an effective amount of -- after "of ".

Column 10,
Lines 19-20, delete "an effective amount".
Line 20, insert -- an effective amount of -- after "of".
Line 26, delete "an effective amount" and substitute therefor -- of effective amounts --.
Lines 33-34, delete "an effective amount" and substitute therefor -- of effective amounts --.
Line 41, delete "an effective amount" and substitute therefor -- of effective amounts --.

Signed and Sealed this

Twenty-third Day of April, 2002

*Attest:*

*Attesting Officer*

JAMES E. ROGAN
*Director of the United States Patent and Trademark Office*